(12) United States Patent
Sarvazyan et al.

(10) Patent No.: US 8,419,643 B2
(45) Date of Patent: Apr. 16, 2013

(54) ULTRASONIC METHOD AND APPARATUS FOR ASSESSMENT OF BONE

(75) Inventors: Armen P. Sarvazyan, Lambertville, NJ (US); Alexej Tatarinov, Riga (LV); Vladimir Egorov, Princeton, NJ (US)

(73) Assignee: Artann Laboratories Inc., Trenton, NJ (US)

( * ) Notice: Subject to any disclaimer, the term of this patent is extended or adjusted under 35 U.S.C. 154(b) by 1973 days.

(21) Appl. No.: 11/533,871

(22) Filed: Sep. 21, 2006

(65) Prior Publication Data

US 2008/0097211 A1   Apr. 24, 2008

(51) Int. Cl.
  *A61B 8/00* (2006.01)
(52) U.S. Cl.
  USPC ........... 600/449; 600/407; 600/437; 600/438; 600/439; 73/599
(58) Field of Classification Search ........... 600/407, 600/437, 438, 449; 73/599
  See application file for complete search history.

(56) References Cited

U.S. PATENT DOCUMENTS

| | | | |
|---|---|---|---|
| 3,847,141 A | 11/1974 | Hoop | |
| 4,421,119 A | 12/1983 | Pratt | |
| 4,474,959 A | 10/1984 | Drury | |
| 4,913,157 A | 4/1990 | Pratt | |
| 4,926,870 A | 5/1990 | Brandenburger | |
| 4,930,511 A | 6/1990 | Rossman | |
| 4,941,474 A | 7/1990 | Pratt | |
| 5,038,787 A | 8/1991 | Antich | |
| 5,143,072 A | 9/1992 | Kantorovich | |
| 5,592,943 A | 1/1997 | Buhler | |
| 5,720,290 A * | 2/1998 | Buhler et al. | 600/449 |
| 5,840,029 A | 11/1998 | Mazess | |
| 5,882,303 A | 3/1999 | Stussi | |
| 6,029,078 A | 2/2000 | Weinstein | |
| 6,086,538 A | 7/2000 | Jorgenssen | |
| 6,135,964 A * | 10/2000 | Barry et al. | 600/449 |
| 6,328,695 B1 | 12/2001 | Vammen | |
| 6,419,632 B1 * | 7/2002 | Shiki et al. | 600/443 |
| 6,468,215 B1 * | 10/2002 | Sarvazyan et al. | 600/438 |
| 6,740,041 B2 | 5/2004 | Faulkner | |
| 2002/0161300 A1 | 10/2002 | Hoff | |
| 2005/0197576 A1 * | 9/2005 | Luo et al. | 600/438 |

* cited by examiner

*Primary Examiner* — Unsu Jung
*Assistant Examiner* — Nasir S Shahrestani
(74) *Attorney, Agent, or Firm* — Boris Leschinsky

(57) ABSTRACT

Methods and apparatus are disclosed for non-invasive bone evaluation based on a broadband ultrasonic transducer emitting a train of ultrasonic wave packets of multiple carrier frequencies ranging from about 50 kHz to about 2 MHz. Receiving broadband ultrasonic transducer accepts broadband ultrasonic signal propagated through the bone. Computer processor provides for data analysis and feature extraction allowing diagnostic evaluation of the bone, including comparing the features of the received signal to a database of known bone conditions.

3 Claims, 20 Drawing Sheets

ULTRASONIC METHOD AND APPARATUS FOR ASSESSMENT OF BONE

REFERENCE TO GOVERNMENT-SPONSORED RESEARCH

This invention was made with government support under grant 5R44AG017400-03 awarded by the National Institute on Aging of the National Institutes of Health and contract NAS3-02167 awarded by the National Aeronautics and Space Administration. The government has certain rights in this invention.

BACKGROUND OF THE INVENTION

This invention relates to a method and apparatus for quantitative assessment of the condition of bones through measurement of spatial profiles of acoustic wave propagation parameters that are sensitive to the bone's material properties, structure, and cortical thickness.

Investigation of mechanical properties of bone and assessment of bone quality is important in view of osteoporosis and for evaluation of bone fracture risk. Osteoporosis presents a common public health problem, becoming increasingly dramatic as the population ages. It affects a large proportion of post-menopausal women and elderly individuals of both genders. Proper treatment can reverse or inhibit the osteoporosis from progressing. Secondary osteoporosis and osteopenia are factors inherent to a variety of metabolic and endocrine disorders that require monitoring during treatment of the primary disease.

Radiological densitometers, including dual-energy x-ray absorption (DEXA) and quantitative computed tomography (QCT) devices are widely used for evaluation of bone density and bone mass, which decrease due to bone resorption in osteoporosis. However, osteoporotic fracture risk cannot be reliably predicted by bone density alone without referring to bone mechanical status, which correlates poorly with radiographic bone density. Planar densitometers provide data on the apparent bone density but do not distinguish between contributions from cortical thickness, which broadly varies among individuals, and from true bone density, affected by porosity and the level of mineralization. Changes in microstructural properties, such as accumulation of micro-damages, are also associated with bone hardness and brittleness. These are yet other factors of bone fracture risk not assessable by DEXA or QCT. Besides those mentioned above there are many other reasons including high cost, lack of portability, and hazardous radiation exposure that altogether limit availability of this technique, encumbering its use in wider screening and monitoring of the at-risk population.

Quantitative ultrasound (QUS) presents an alternative to X-ray densitometry, possessing several advantages such as:
1) providing information on the elastic properties and structural changes (porosity) of bone, which is not assessable by DEXA;
2) posing no irradiation hazard, allowing radiation-safe and off-repeated measurements;
3) allowing portability, ease of use and lower costs.

Ultrasound velocity directly depends on the bulk elasticity modulus of bone. Ultrasound attenuation, which is another important QUS parameter, reflects structural changes during osteoporosis as manifested by a decrease of trabecular density.

It is known that osteoporosis and osteopenia result in degradation of bone quality. There are two major contributors to poor bone quality:

1) factors that determine quality of the bone material, such as increased porosity, changes in mineralization, accumulation of micro-damages, etc. and
2) internal resorption dominating over bone remodeling, which ultimately leads to bone thinning.

Osteoporosis fracture risk is caused by both of these factors acting separately or together causing worsening of mechanical characteristics and durability of bones. In long bones, increased progress of resorption takes place mainly from the endosteal surface expanding towards the periosteum, therefore causing trabecularization of inner layers of the compact bone and a decrease in the effective thickness of the cortex. Ultrasonic waves applied to the bone in axial propagation mode at a frequency of about 1 MHz are typically used for the assessment of material properties related to mineralization and porosity developing within the cortex (see for example Bossy E, Talmant M, Peyrin F, Akrout L, Cloetens P, Laugier P. An in-vitro study of the ultrasonic axial transmission technique at 1 MHz velocity measurements demonstrated sensitivity to both mineralization and intracortical porosity. *J Bone Miner Res.* 2004; 19(9): 1548-56). Assessment of cortical thickness is possible by application of guided waves in a lower frequency band, in which velocity is a function of the ratio of thickness to wavelength (see for example Lee K I, Yoon S W. Feasibility of bone assessment with leaky Lamb waves in bone phantoms and a bovine tibia. *J Acoust Soc Am.* 2004; 115(6):3210-7).

Another approach uses a pulse-echo mode and autocorrelation analysis of the signals reflected from inner and outer surfaces of the cortex (Wear K A. Autocorrelation and cepstral methods for measurement of tibial cortical thickness, *IEEE Trans Ultrason Ferroelectr Freq Control.* 2003; 50(6): 655-60). Guided acoustic waves have been demonstrated to be informative about the biomechanical properties of bones in vitro, detecting manifestations of osteopenia in model studies on phantoms (Tatarinov A, Sarvazyan A. Dual-frequency method for ultrasonic assessment of bones: model study. *Proc. World Congr. Ultrasonics*, WCU 2003, Paris, 895-898) and discriminating osteoporosis patients with higher resolution when compared with the use of longitudinal acoustic waves (Nicholson P H, Moilanen P, Karkkainen T, Timonen J, Cheng S. Guided ultrasonic waves in long bones: modeling, experiment and in vivo application. *Physiol Meas.* 2002; 23(4):755-68).

A number of U.S. patents disclose through transmission ultrasonometers, generally applied to the bilaterally accessible bones such as a heel. U.S. Pat. No. 3,847,141 for example describes an ultrasonometer, which measures ultrasound propagation parameters by transmitting and receiving an acoustic signal using narrowband transducers positioned at the opposite sides of a bone. Systems disclosed in U.S. Pat. Nos. 4,421,119, 4,474,959, 4,913,157, 4,926,870, 4,930,511, 4,941,474, and 5,592,943 operate with ultrasonic longitudinal waves in broadband range and in the analysis of recorded acoustic signals. These systems make use of both the changes in the ultrasonic spectra and in the temporal propagation parameters. The systems differ by the manner of acoustic coupling of the transducers to the patient's body, calibration procedures and data processing algorithms. U.S. Pat. Nos. 5,840,029 and 6,086,538 describe ultrasonometers providing measurements at a number of spatially separated locations on the bone to identify a region of interest thereon.

Other known ultrasonic techniques for characterization of bones include measurements of ultrasound reflection from the bone at various angles of incidence as described for example in U.S. Pat. No. 5,038,787. Another known system determines attenuation from reflected signals as described in U.S. Pat. No. 6,328,695. Another yet example of such system combines a non-linear analysis and evaluation of shear wave propagation parameters, as described in U.S. Patent Application No. 20020161300. For more sensitive assessment of osteoporosis and bone fracture risk, some authors combine ultrasonic, densitometric and other data, as described in U.S. Pat. Nos. 6,029,078, and 6,740,041.

Assessment of bone by unilateral measuring the velocity of ultrasonic waves traveling along the bone is described in U.S. Pat. Nos. 5,143,072 and 6,328,695. In U.S. Pat. No. 5,143,072 a system is proposed that has two receivers positioned co-linearly to measure the propagation velocity by time increment between the receivers, therefore eliminating the error caused by delay of the sound pulse in soft tissue. In U.S. Pat. No. 6,328,695, the error of ultrasound velocity in bone measurement due to the presence of soft tissue layer is accounted for by making separate pulse-echo measurements of the ultrasound delay in the soft tissue layer. In both cases, a longitudinal ultrasonic wave is used, the velocity of which is a function mainly of the bone material elasticity modulus.

Application of guided stress waves for evaluation of the bone firmness is described in U.S. Pat. No. 5,882,303. The guided waves are generated by hammering impacts. The transmission function referring to pulse width and height is acquired at a number of set points along the bone. Being potentially good indicators of the total bone rigidity determined by both the bone geometry and material stiffness, these parameters do not discern between the above mentioned factors and, besides, could be influenced by numerous random factors such as individual anatomical variations.

A method and device for multi-parametric ultrasonic assessment of bone conditions are proposed in U.S. Pat. No. 6,468,215, where combined application of the longitudinal wave and quasi-flexural mode of guided waves is described. The patent also describes the stepped scanning procedure along the bone trajectory and presentation of measured ultrasonic parameters as axial profiles. The axial profiles can serve as a measure of spatially developing processes in bones and individual characteristics of these processes among patients. However, the method and the device described in U.S. Pat. No. 6,468,215 have the following major shortcomings:

1) Excitation of different wave modes is achieved using the first and third harmonics of a resonant piezoelectric transducer. Generation and receiving of ultrasound waves by such resonant narrow band transducers does not allow making measurements with short ultrasonic pulses. When the received pulse is long, it requires a much longer distance between the transmitter and the receiver to have the arrival of different modes of acoustic waves separated in time. It is hard to realize sufficiently long acoustic base because of anatomical limitations and significant attenuations of ultrasonic waves in bone. Use of narrow band transducers does not allow flexibility in varying the carrier frequency of ultrasonic waves, which is necessary for obtaining data on propagation parameters of various modes of acoustic waves in the bone;

2) Only a fraction of diagnostically relevant information that is present in the received ultrasonic waveforms is analyzed. Although ultrasound propagation parameters, such as velocity, attenuation, and their frequency dependences are informative characteristics, the calculation of these parameters is based on numerous poorly based assumptions. This can be avoided if the diagnostic information is directly extracted from the received acoustic waveforms, which is not envisioned in the method described in the patent.

The need therefore exists for an improved device, data acquisition, and processing methods for the axial testing of long bones and development of additional parameters for sensitive assessment of bone conditions.

SUMMARY OF THE INVENTION

The object of the present invention is to provide a method and apparatus for assessment of bone based on comprehensive analysis of waveforms of ultrasound signals propagating in the bone. A set of ultrasound propagation parameters, which are differentially sensitive to the material properties, structure, and cortical thickness of the bone are evaluated. The parameters include various features of different types of ultrasonic waves, such as bulk (also referred to as longitudinal), surface and guided waves, obtained in a wide range of carrier frequencies, as well as signal spectral and power derivatives. The invention includes data processing algorithms for obtaining axial profiles of waveform parameters revealing axial heterogeneity of long bones.

The method generally includes the steps of:
1) positioning of a pair of broadband transducers, one of which is an emitting transducer and the second one is a receiver, on the bone surface unilaterally along the bone axis or other predetermined trajectory;
2) emitting a train of ultrasonic wave packets of multiple carrier frequencies in the range from 50 kHz to 2 MHz and acquiring ultrasonic signals passed along the examined bone by the receiver;
3) repeating steps 1 and 2 at multiple points along the predetermined trajectory of scanning;
4) analyzing acquired ultrasonic signals and determining portions of acquired waveforms related to different modes of ultrasonic waves identified as longitudinal, surface, and guided waves;
5) plotting axial profile graphs for selected features of the acquired waveform along the examined trajectory;
6) analyzing the acquired waveform parameter profiles for different wave modes and frequencies;
7) correcting these profiles by mathematical filtering and image proceeding algorithms in order to avoid random errors due to improper manipulation of the probe; and finally
8) comparing waveform parameter profiles with statistical reference data and evaluating the level of abnormality or similarity to known bone pathologies.

The examination procedure may include either one long bone of the skeleton like the tibia, radius of the forearm, etc. or several bones in sequence to form a comprehensive diagnosis over different parts of the skeleton.

To provide ultrasonic responses at multiple carrier frequencies in a broadband range from about 50 kHz to about 2 MHz, a train of short excitation pulses (wave packets) are applied. Each short excitation pulse is composed of a few periods of a harmonic signal.

The method is based on the exploitation of propagation parameters of different wave modes, between which the energy of ultrasound in bone is distributed. Such wave modes include:

1) the low-frequency guided wave, in which the wavelength is greater than the bone cortical thickness and therefore the geometrical dispersion of velocity is observed,
2) the high-frequency longitudinal wave, in which the wavelength is smaller or comparable with the bone cortical thickness, propagating in the sub-surface layer of the bone, and 3) the high-frequency surface wave or Rayleigh surface wave.

Another object of the present invention is to enable reliable identification of the waveforms corresponding to the aforementioned wave modes, and to provide measurements pertaining to identical reference points in the waveform of a particular acoustical mode measured at neighboring locations.

The present invention also provides for method of assessment of expressed natural topographical heterogeneity of acoustical properties in long bones and spatially non-uniform pathological processes, such as osteoporosis.

The initial signal acquisition file is composed of a series of recorded waveforms presented as a two-dimensional (2-D) map, where the X-coordinate is time and the Y-coordinate is the distance along the scanned trajectory. The values in the 2-D map are the amplitudes of ultrasonic signals in a relative scale. This 2-D pattern (waveform parameters map) is further refined by image processing algorithms. The processing algorithms applied to the 2-D waveform map include sequential smoothing of the patterns by various low-pass filters and selection of axial profiles of the waveform parameters.

In the received waveform, the arrival time of the slower types of waves—guided and surface waves—are masked by the signal from the fast longitudinal waves. Separation of these waves can be achieved by wavelet analysis. In certain predetermined time interval, the central peak of the wave packet of the guided or surface wave mode is determined by the maximum of the wavelet function similar to the wavelet function for the corresponding excitation waveform. To minimize an error in evaluation of the position of the wavelet function maximum, intensities of several consequential signals along the bone length are added up and averaged, with the resulting central peak being defined as the true maximum.

To minimize error caused by operator manipulations, the sequence of discrete readings along the bone is approximated by a smooth curve. It is assumed that changes in bone thickness and mechanical properties occur smoothly along the bone length and random fluctuations of readings may occur only due to measurement and scanning errors. The standard deviation of the approximation curve is calculated for each point along the bone. The sum of the standard deviations is qualified as a "quality index" for the investigation procedure, providing a basis to accept or reject the measurement results.

The invention involves evaluation of numerous acoustic parameters that can reflect changes of bone properties and structure. These parameters are related to the wave packet spectral changes, such as center frequency shift and ratio of signal amplitudes at low and high frequencies. The frequency shift is defined as a difference between the center frequency of the transmitted signal and that for the received signal portion found by wavelet analysis in the frequency domain. The center frequency shift is displayed as a profile graph to serve as an indicator of possible local changes in bone structure. Maximum intensities of wave packets related to the longitudinal (bulk), surface, and guided waves at low and high frequencies are found as peak amplitudes of the corresponding wavelet envelopes. The intensity ratios also are presented as profile graphs along the bone length and such profiles are sensitive to the spatial heterogeneity of the bone.

The invention involves processing of 2-D waveform parameter maps through the following steps:
1) interpolation and 2-D filtering to reduce errors and noise;
2) normalization by peak amplitude in every line to provide for more uniform waveform parameter maps that are less dependent on fluctuations of contact conditions during probe application at each consecutive measurement during one measurement;
3) rectification of ultrasonic signals;
4) selection of a region of interest related to the most diagnostically informative area of the waveform parameter maps;
5) low pass filtering;
6) application of amplitude thresholds to detect arrival time of front of a particular mode of acoustic wave in the received signal; and finally
7) image balancing to present waveform maps in the regions of interest as visual pictures characterizing the bone quality.

Quantitative parameters derived from the processing of 2-D waveform maps used to detect and characterize conditions of bones include:
1) arrival times of various types of acoustic wave fronts determined at certain relative amplitude thresholds in several zones along the bone length;
2) average or integral signal intensities in informative sub-regions of the waveform parameter map; and
3) a proximity index as a measure of correlation of an individual waveform parameter map with a reference map from the database relating waveform parameter maps to diagnostically specified conditions of bone (i.e. expressed osteoporosis).

In one embodiment of the method, the signals acquired by the receiving transducer are related to corresponding transmitted signals and the transfer function for every point of measurement along the scanning trajectory is calculated. The transfer function contains comprehensive information about a plurality of parameters of various modes of acoustic waves propagating in the tested site of the bone. The spatial profile of the acoustic transfer function is then used for assessment of the tested bone by correlating it with corresponding transfer functions from the database developed based on systematic statistical data obtained in clinical studies.

The invention includes an apparatus realizing the above described method comprising a hand-held ultrasonic scanning probe, an electronic unit for excitation and acquisition of ultrasonic signals, and a computer to serve as a processor and display.

Ultrasonic hand-held scanning probe is provided for obtaining a sequence of ultrasonic responses from the bone in multiple locations along the bone. It is comprised of emitting and receiving ultrasonic transducers, a preamplifier for amplifying the received ultrasonic signals, and a positioning means. Broadband non-resonant ultrasonic transducers are used for excitation of short ultrasonic packets in a broad frequency range and receiving the responses from bone containing different modes of acoustic waves. The positioning means can be a simple tape or template with a plurality of predetermined markings to indicate the locations of measurement along the chosen before trajectory over the tested bone. Alternatively, it can be a distance meter. In one embodiment of the device, the distance meter includes a roller tracking along the surface of the examined bone, and an electrical counter that measures the tracked distance. A light emitting diode mounted on the probe provides feedback to the operator indicating the intensity of the received ultrasonic signal to ensure necessary contact pressure for obtaining reliable data.

The electronic unit is equipped with the means to perform many functions, such as:
1) generating excitation waveforms downloaded from a computer, 2) acquiring received ultrasonic signals traveled along the bone that are synchronized with the emitted signals, 3) synchronizing ultrasonic measurements with the data on the probe position over the bone, and 4) providing means for data exchange with the computer through USB or Ethernet cable with the exchange speed sufficient for real-time feedback.

The advantages of the present invention are significant improvements in the accuracy of diagnostics of osteoporosis and the prediction of fracture risk. Greater sensitivity of the proposed method over that of conventional axial QUS is achieved due to the simultaneous use of multiple acoustic wave modes in a wide frequency band, followed by evaluating of multiple parameters of the received waveforms and analyzing spatial profiles of these parameters, as they characterize both the material properties and thickness of the bone and are sensitive to changes in the cortex and under-cortex spongeous bone.

BRIEF DESCRIPTION OF DRAWINGS

The invention is described in detail thereafter in connection with the schematic drawings in which.

DETAILED DESCRIPTION OF THE INVENTION

Figure 1:
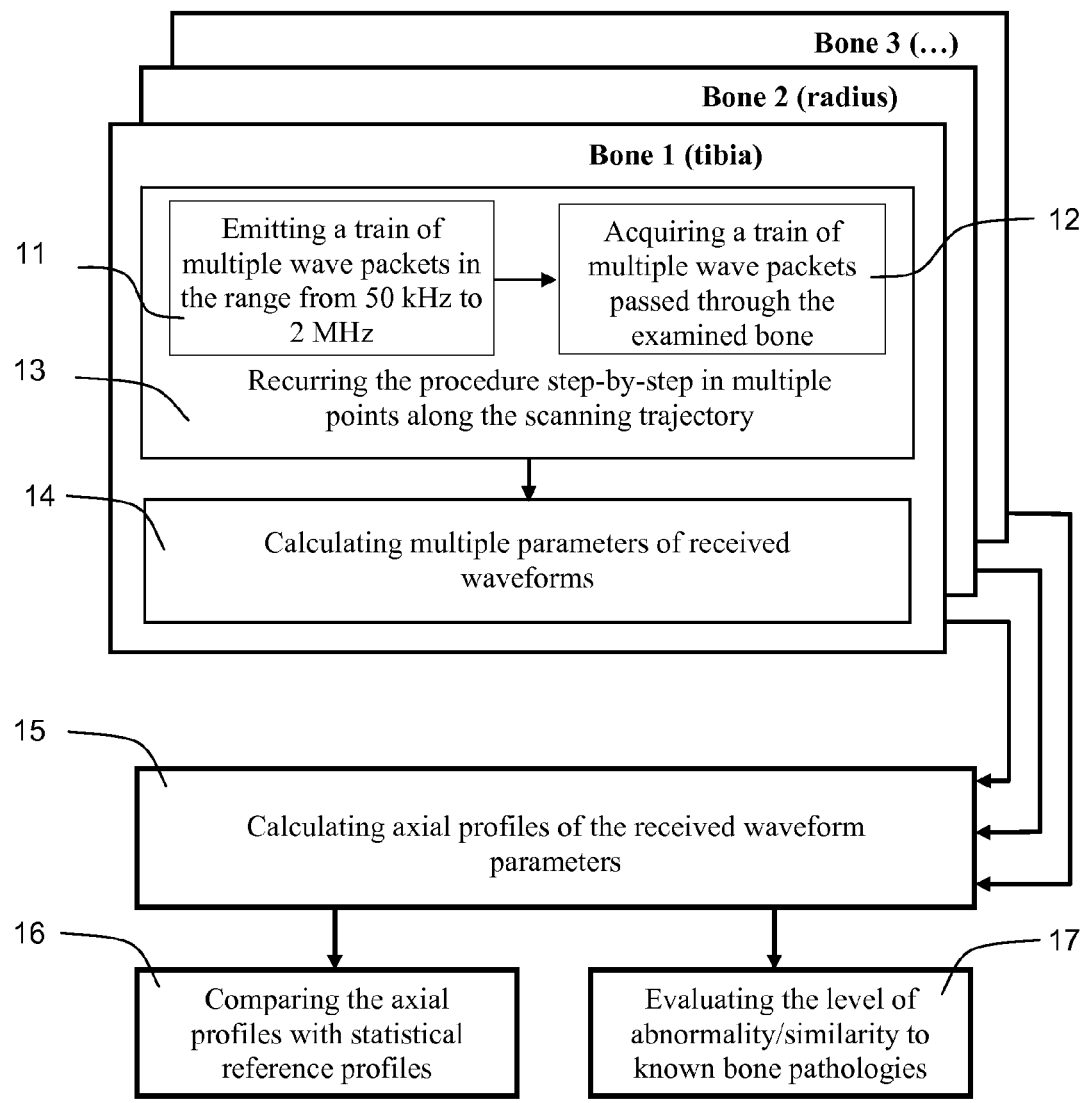
FIG. 1 is a flow chart of the method for assessment of bone conditions based on calculating multiple parameters of received waveforms according to the present invention.

A more complete appreciation of the invention and many of the advantages thereof will be accomplished by reference to the following description when considered in connection with the accompanying drawings. Wherever possible, the same reference numerals will be used throughout the drawings and descriptions to refer to the same or like parts.

FIG. 1 is a flow chart illustrating the main steps and procedures of the method for non-invasive and quantitative assessment of bone conditions according to the present invention.

As illustrated in FIG. 1, this method refers to the following specific exemplary steps taken for each evaluated bone:

1) 11—emitting a train of multiple wave packets in the ultrasonic frequency range from 50 kHz to 2 MHz by the emitting transducer;

2) 12—acquiring a train of ultrasonic pulses of multiple frequencies passed along the examined bone by the receiving transducer and recording the received waveforms;

3) 13—repeating the measurement at multiple points along the predetermined trajectory of scanning;

4) 14—calculating the waveform parameters for ultrasonic signals related to different modes of ultrasonic waves identified as longitudinal (bulk), surface, and guided waves;

5) 15—plotting axial profiles of waveform parameters;

6) 16—comparing the axial profiles with statistical reference data; and 7) 17—evaluating the level of abnormality or similarity to known bone pathology.

Steps 11-17 may be carried out in available zones of several types of long bones like the tibia, radius, ulna etc. to provide more comprehensive diagnostics of bone condition.

Figure 2:
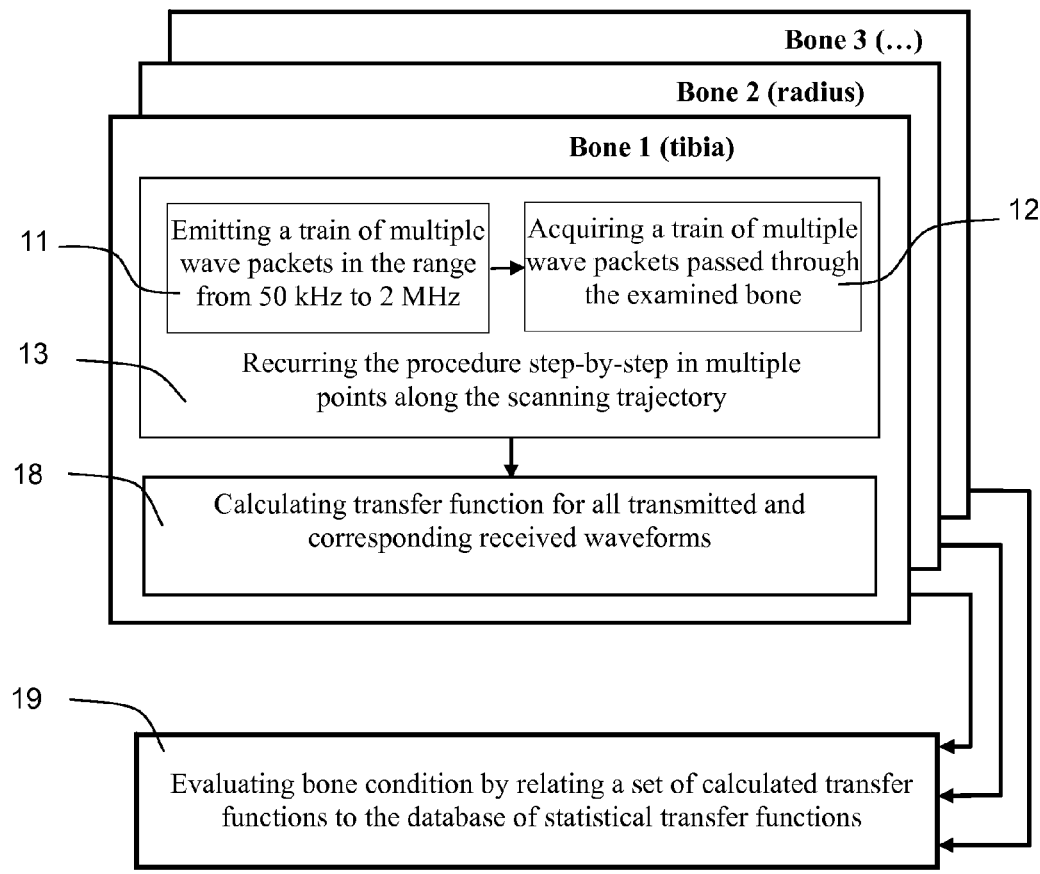
FIG. 2 is a flow chart of a method for assessment of bone conditions based on the use of plurality of transfer functions for all transmitted and corresponding received waveforms according to the present invention.

FIG. 2 is a flow chart illustrating another method for non-invasive and quantitative assessment of bone conditions according to the present invention, which has the same initial steps and procedures coinciding with those of the method illustrated in FIG. 1 but instead of steps 14-17 it adds steps 18 and 19. In the step 18, the signals acquired by the receiving transducer are related to corresponding transmitted signals and the acoustic transfer function for every point of measurement along the scanning trajectory is calculated. The acoustic transfer function contains comprehensive information on plurality of parameters of various modes of acoustic waves propagating in the tested site of the bone. In the step 19, the spatial profile of the acoustic transfer functions is used for assessment of the tested bone by correlating it with corresponding transfer functions from the database developed using systematic statistical data obtained in clinical studies.

Figure 3A:
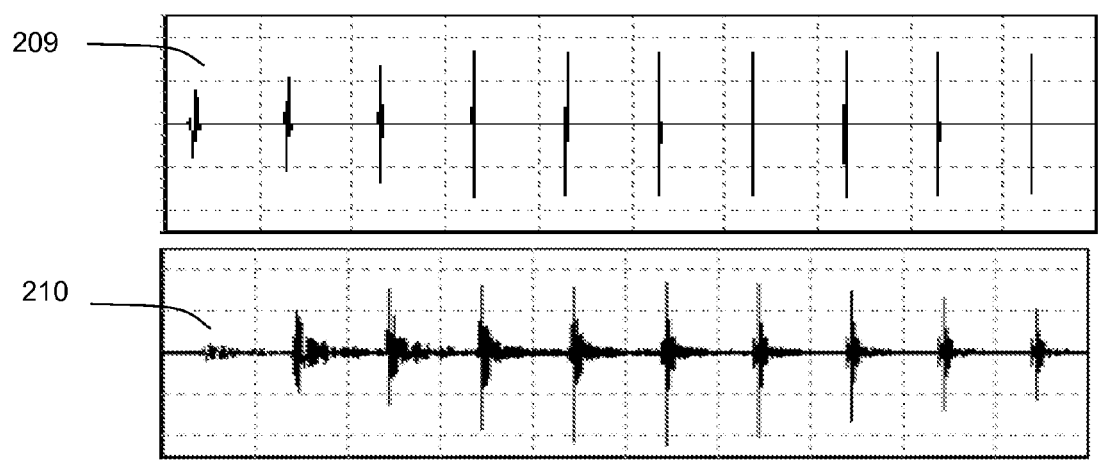
FIG. 3A shows a train of transmitted ultrasound pulses of multiple frequencies and corresponding train of acquired pulses during one cycle of measurement.

FIG. 3A shows an example of a train of transmitted ultrasound pulses of multiple frequencies 209 and corresponding train of acquired pulses 210 during one cycle of measurement. The transmitted train 209 comprises ultrasonic pulses with carrier frequencies of 0.1, 0.2, 0.3, 0.4, 0.5, 0.6, 0.7, 0.8, 0.9, and 1.0 MHz. The acquired train of pulses 210 was obtained on tibial diaphysis of a young healthy male.

Figure 3B:
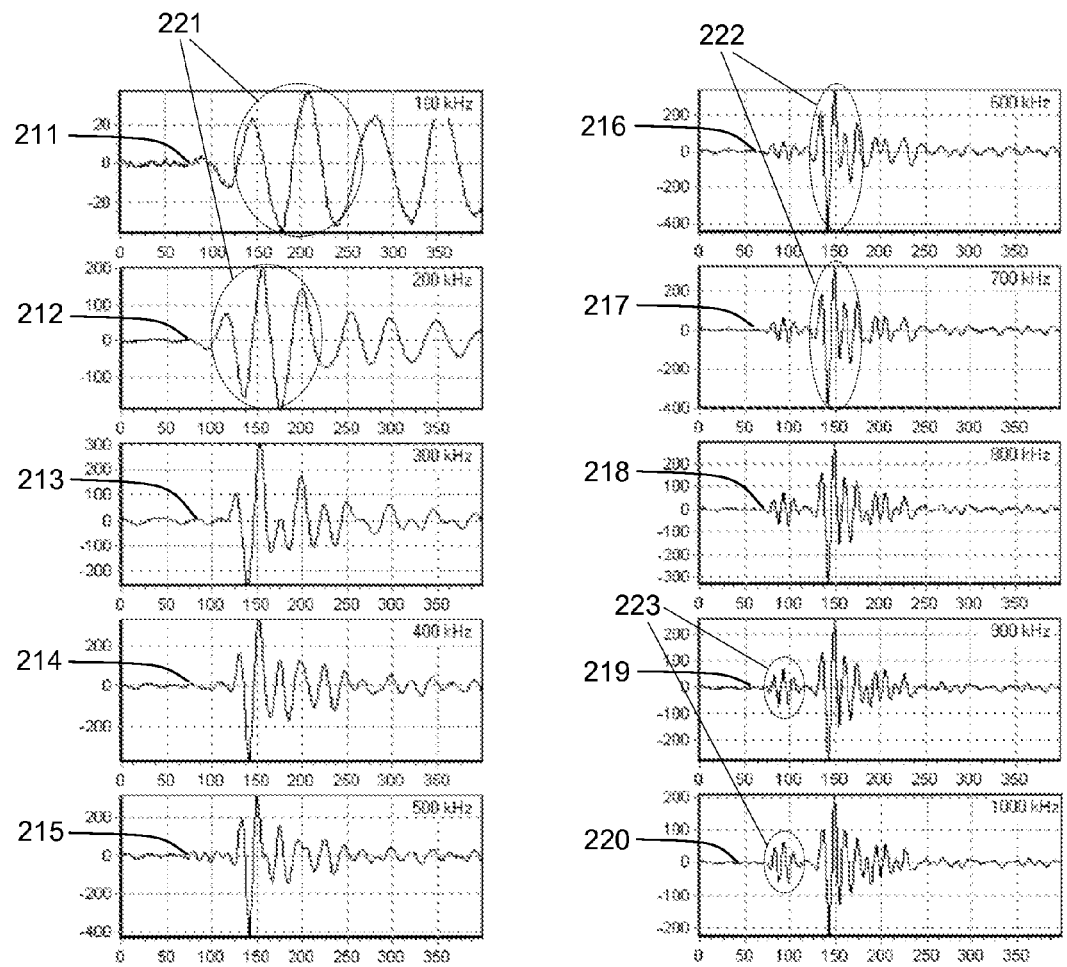
FIG. 3B shows a sequence of received signal waveforms at multiple frequencies received on tibial diaphysis of a healthy male.

FIG. 3B shows close-ups of separate ultrasonic pulses 211-220 of the acquired train 210 shown in FIG. 3A. The sequence of received signal waveforms 211-220 at multiple frequencies in the range of 100 kHz-1 MHz was obtained on tibial diaphysis of a healthy male. Different types of acoustic waves become apparent at different frequencies and can be identified as bulk waves 223 (the fastest wave component at high frequencies); surface waves 222 (the slower wave component of greater amplitude at high frequencies) and guided waves 221 (the dominant wave component at low frequencies).

Figure 4:
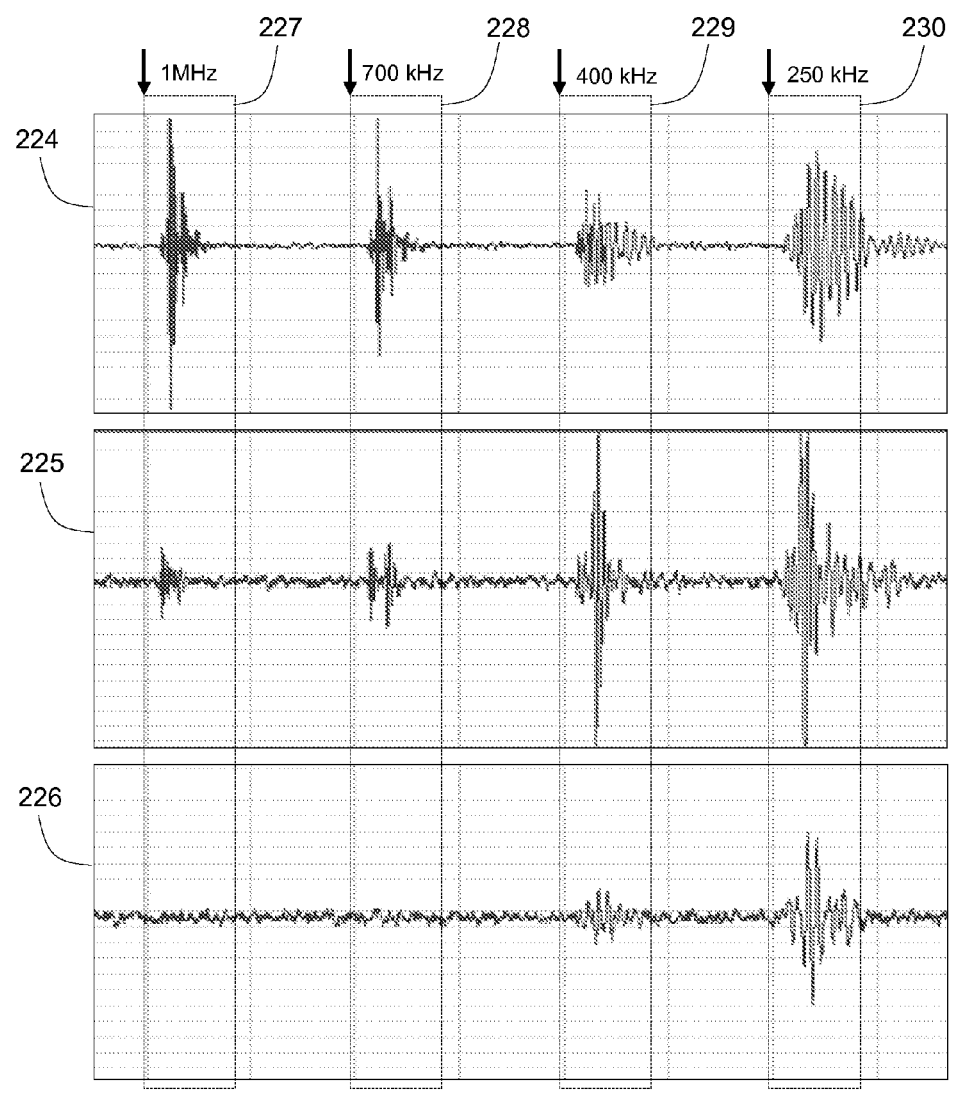
FIG. 4 shows gradual changes of ultrasonic signal at different frequencies in 0.25-1 MHz band in 4 mm thick double-layered phantoms with increasing porosity.

FIG. 4 shows typical changes in the received ultrasonic waveforms 227-230 in bone phantoms with varying cortical thickness and porosity level at different frequencies in 0.25-1 MHz band. Composite two-layer phantoms modeling advanced porosity in deep lying bone layers from which osteoporosis progresses were measured. The pores were mimicked by water soaked poppy seeds embedded in the epoxy. Thicknesses of the layers were 2.5 mm solid/1.5 mm porous (panel 224), 1.5 mm solid/2.5 mm porous (panel 225), 3.5 mm/0.5 mm porous (panel 226). Gradual substitution of the solid layer by the porous one results in redistribution of ultrasound energy between various acoustic wave modes in the received signal. Experimental data clearly shows dramatic changes in the spatio-temporal parameters of signals at every one of the tested frequencies upon variations of cortical thickness and porosity, quantitative evaluation of which is the key issue in osteoporosis assessment.

Figure 5:
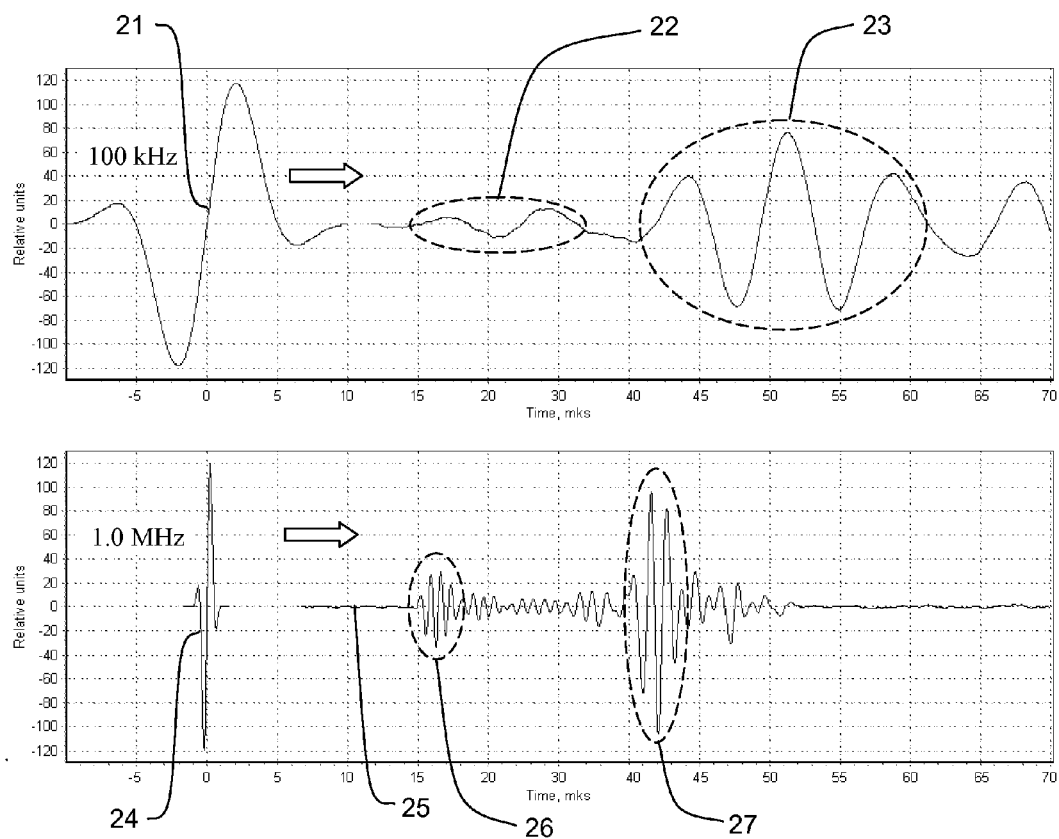
FIG. 5 shows exemplary emitted and acquired low-frequency (100 kHz) and high-frequency (1.0 MHz) signals in the part of the tibia containing predominantly compact bone.

FIG. 5 shows low-frequency excitation signal 21 and high-frequency excitation signal 24 positioned on the same time scale with corresponding ultrasonic response signals obtained from bone in areas containing predominantly compact tissue. Typical signals in the tibia middle shaft are presented as an example. The following portions of ultrasonic signals passed through the bone are analyzed and used for wave profile calculation:
1) for the low-frequency signal, a portion 22 (or the first wave packet) and a portion 23 characterized by maximum intensity and related to the guided wave,
2) for the high-frequency signal, a portion of 26 related to the bulk wave and the slower portion 27 of greater amplitude related to the surface wave is analyzed. A predetermined time interval 25 preceding the arrival of first signal is used for calculating noise levels as control references for the electronic measurement circuit.

Figure 6:
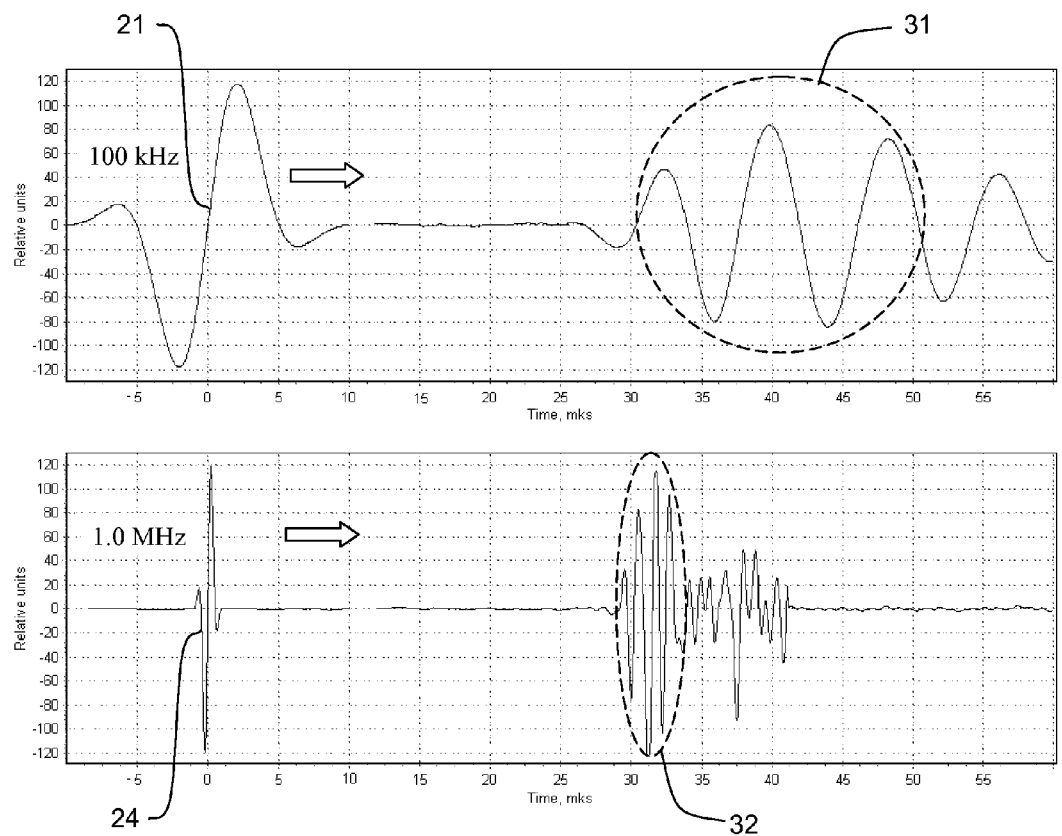
FIG. 6 shows exemplary emitted and acquired low- and high-frequency signals in the part of the tibia containing predominantly spongeous bone.

FIG. 6 shows low-frequency excitation signal 21 and high-frequency excitation signal 24 positioned on the same time scale with corresponding ultrasonic response signals obtained from bone in areas containing predominantly spongeous tissue. Typical signals in the tibia epiphisis are presented as an example. At both low and high frequencies, due to a thin cortex, maximum energy of the wave packets corresponds to the bulk wave or longitudinal sub-surface wave propagating in the spongeous bone. The corresponding portions of low-frequency and high-frequency signals 31 and 32, respectively, related to the bulk wave are used in this case for parameters calculation.

Figure 7:
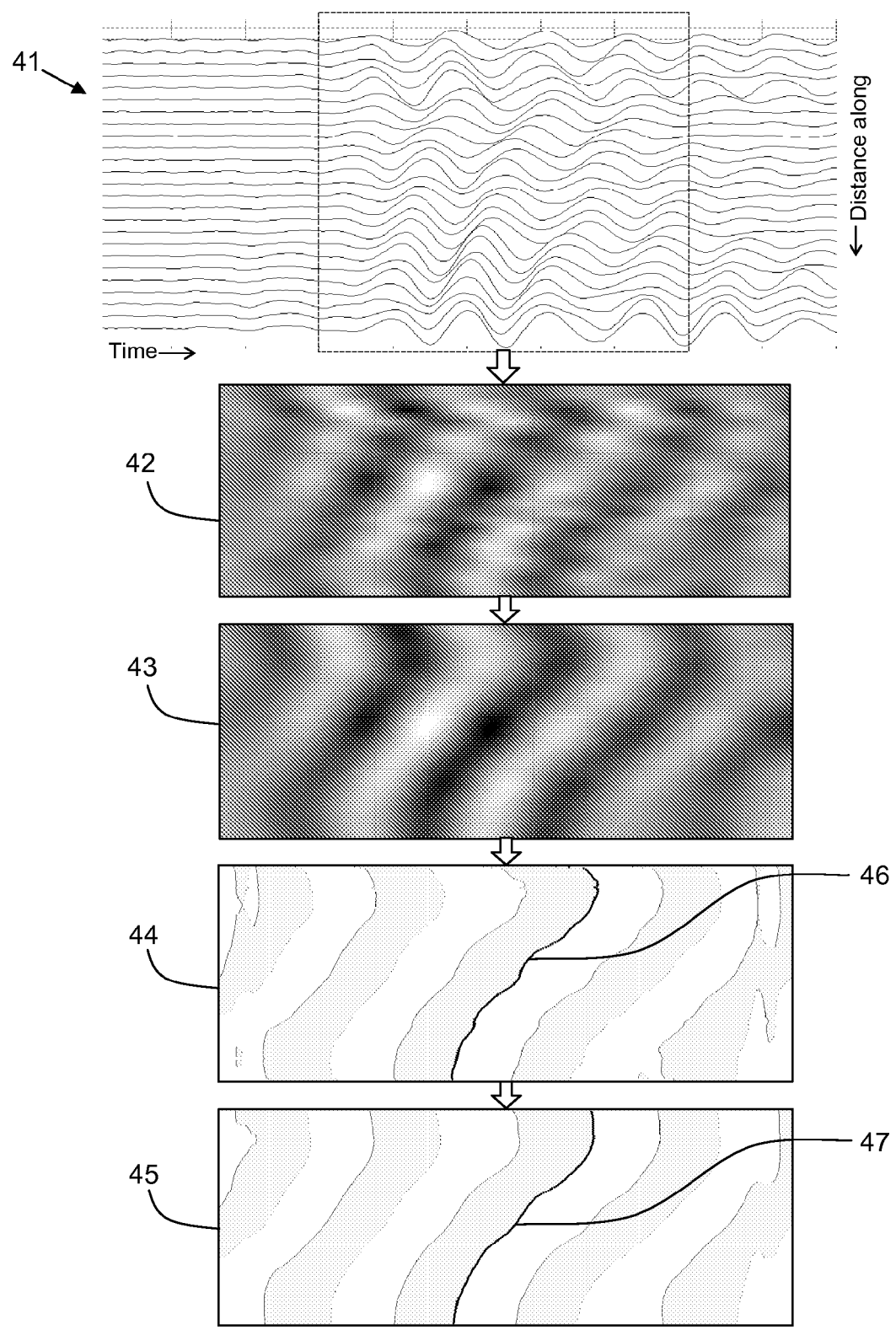
FIG. 7 shows the steps in the evaluation of a phase profile by processing the 2-D map of acquired waveforms, where the vertical coordinate is distance along the scanned bone and the horizontal coordinate is time.

FIG. 7 illustrates the steps in composing the waveform parameter profile by processing a 2-D map of acquired ultrasonic signals 41 obtained by stepwise scanning the probe along a bone. At first, the 2-D signal map 42 is constructed from initial ultrasonic signals 41, where the vertical coordinate is distance along the scanned bone and the horizontal coordinate is time. Signal amplitudes are depicted by the gray scale of the image. Every horizontal line in 2-D signal map 42 corresponds to a single ultrasonic signal recorded at a specified distance along the bone from a starting reference point. Further, 2-D signal map 42 is processed by smoothing using rectangular and Gaussian filters to eliminate random deviations and to obtain smoothed 2-D signals map 43. In the next step, the image binarization is performed and 2-D map 44 is produced, where signal intensities below or above a predefined threshold allow separating a narrow border line 46 characterizing the wave profile. Additional filtering applied to map 44 provides smoothed binary map 45 and wave phase profile 47.

Figure 8:
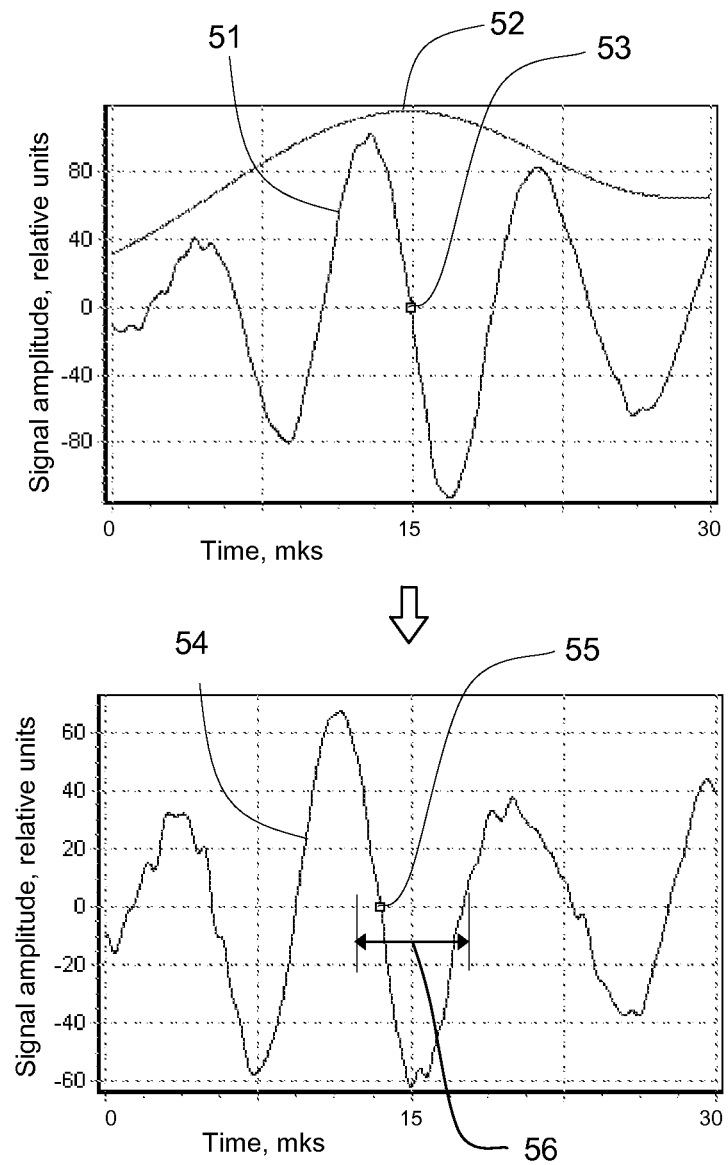
FIG. 8 is an illustration of using the wavelet technique to detect the time position of an acquired wave packet at a predetermined site of examined bone so as to capture a reference phase in the acquired waveform to further calculate the time position and profile of said reference phase along the length examined bone.

FIG. 8 is an illustration of using the wavelet technique to detect times-of-flight for the low-frequency guided wave. Initial signal 51 is processed by complex wavelet functions having waveforms similar to the excitation signal, and the maximum of calculated wavelet modulus 52 is detected. Estimating the temporal position of this maximum allows calculating the group velocity of the wave packet. This algorithm is also used to choose certain reference phase and track this reference phase for the same wave packet in every successive measurement point along the scanning trajectory. The temporal position of the zero intersection point 53 on the negative slope of the signal 51, nearest to the position of the wavelet modulus maximum 52, is calculated. The signal 54 recorded at the next measurement point along the scanning trajectory is analyzed and zero-intersection point 55 is detected by the same method as the point 53. A specified time interval 56 around the point 53 provides a range to search for the zero-intersection point 55. If point 55 is located outside the interval 56, it is rejected and the next measurement point along the bone is analyzed relative to the interval 56. If point 55 is located inside the interval 56, it is considered correct. This constraint helps to eliminate erroneous measurement data and makes the wave phase axial profile calculation more robust.

Figure 9:
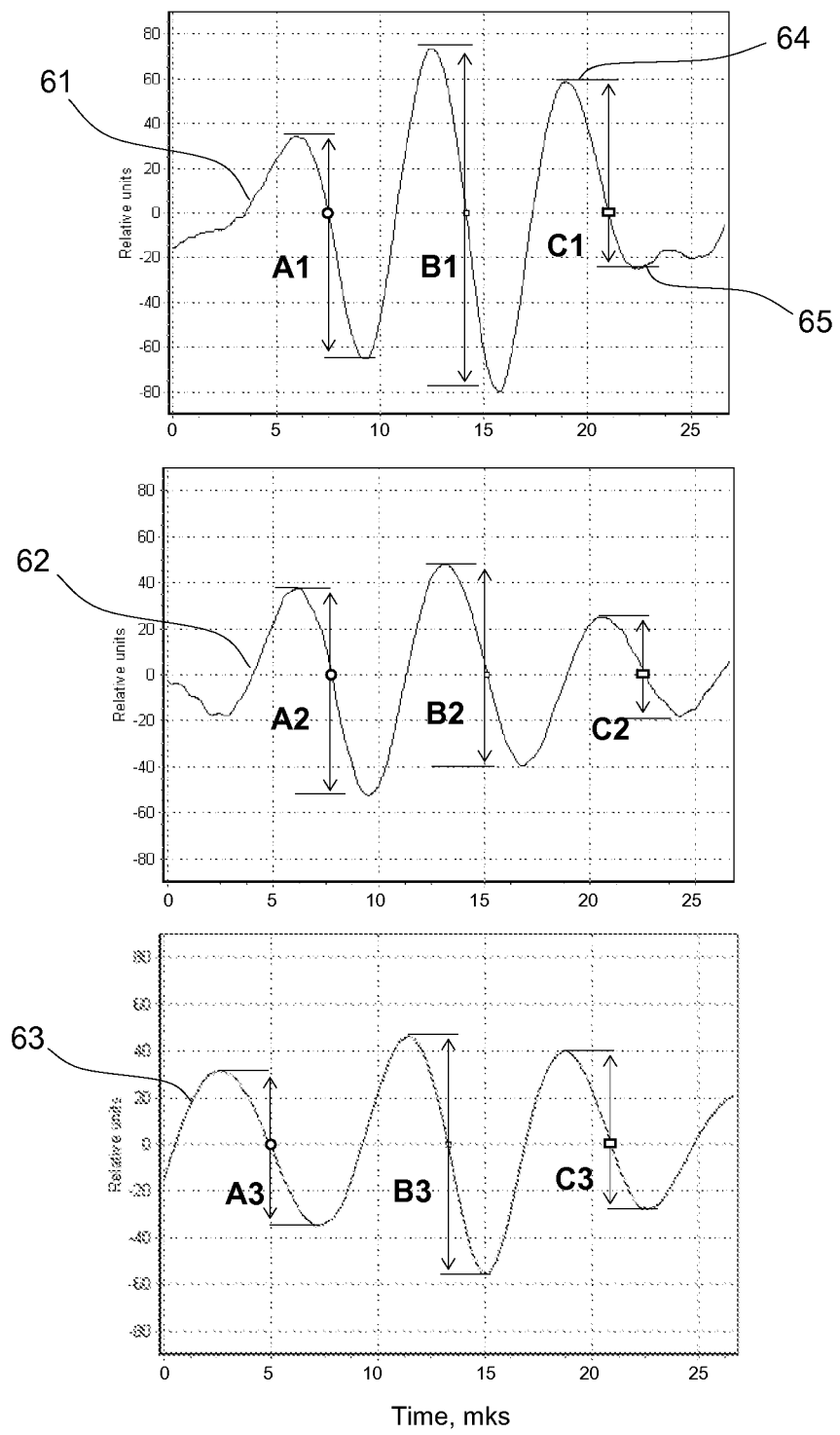
FIG. 9 is an illustration of an algorithm for detection of the received signal true maximum.

FIG. 9 is an illustration of signal strength calculations used as an algorithm for detection of a true signal maximum when the wave maximums fluctuate among signals in adjacent points along the bone due to measurement errors and noise of various origins. Signals 61, 62, and 63 are ultrasonic signals at adjacent measurement points along the bone with zero-crossing points A, B, C related to adjacent wave maxima. To identify zero-intersection point in each ultrasonic signal, the algorithm presented above in the description of FIG. 8 is used. The signal strength calculation algorithm includes the steps of determination of amplitude span around the zero-interception points A, B, and C. Nearest maximum and minimum around the corresponding point on each period of the waveform are detected, such as maximum 64 and minimum 65 around point C1. The sum of the amplitude spans for A1-A3, B1-B3, and C1-C3 are calculated and the largest sum represents the maximum signal strength. This procedure is applied to all measurement points along the bone.

Figure 10:
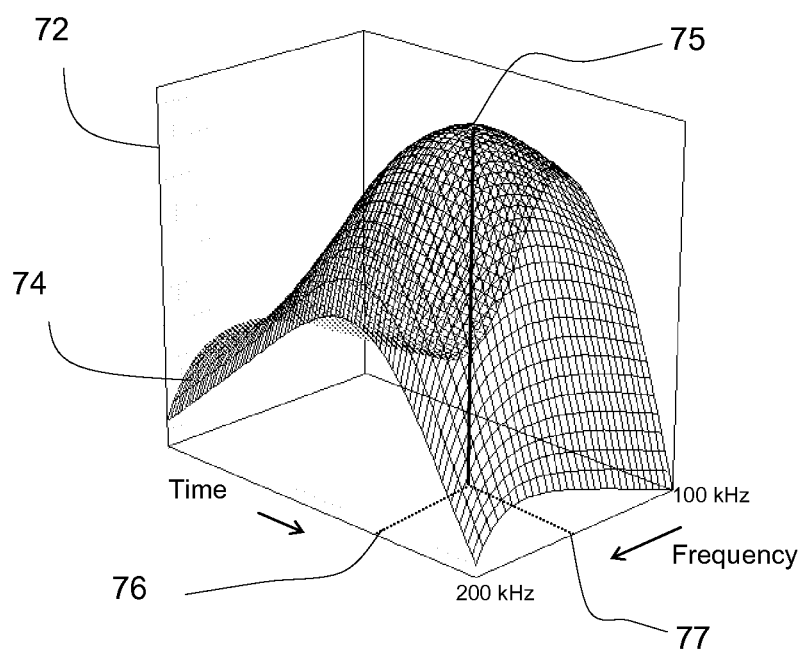
FIG. 10 is an illustration of employing the wavelet technique to detect the time position of the acquired wave packet and a center frequency of this wave packet corresponding to the maximum value of wavelet modulus.

FIG. 10 illustrates the use of a wavelet technique for detecting both the temporal position and the center frequency of acquired wave packet passed through a bone. Panel 72 shows a 3-D surface 74 representing a wavelet modulus function along time coordinate calculated for the frequencies ranging from about 100 kHz to about 200 kHz. The vertical axis is the normalized amplitude of wavelet modulus applied to the analyzed wave packet. The projection of the maximum amplitude 75 determines the temporal position 76 and the center frequency 77 for the wave packet. A frequency shift is defined as a difference between the center frequency of the acquired wave packet and the center frequency of the emitted pulse.

Figure 11:
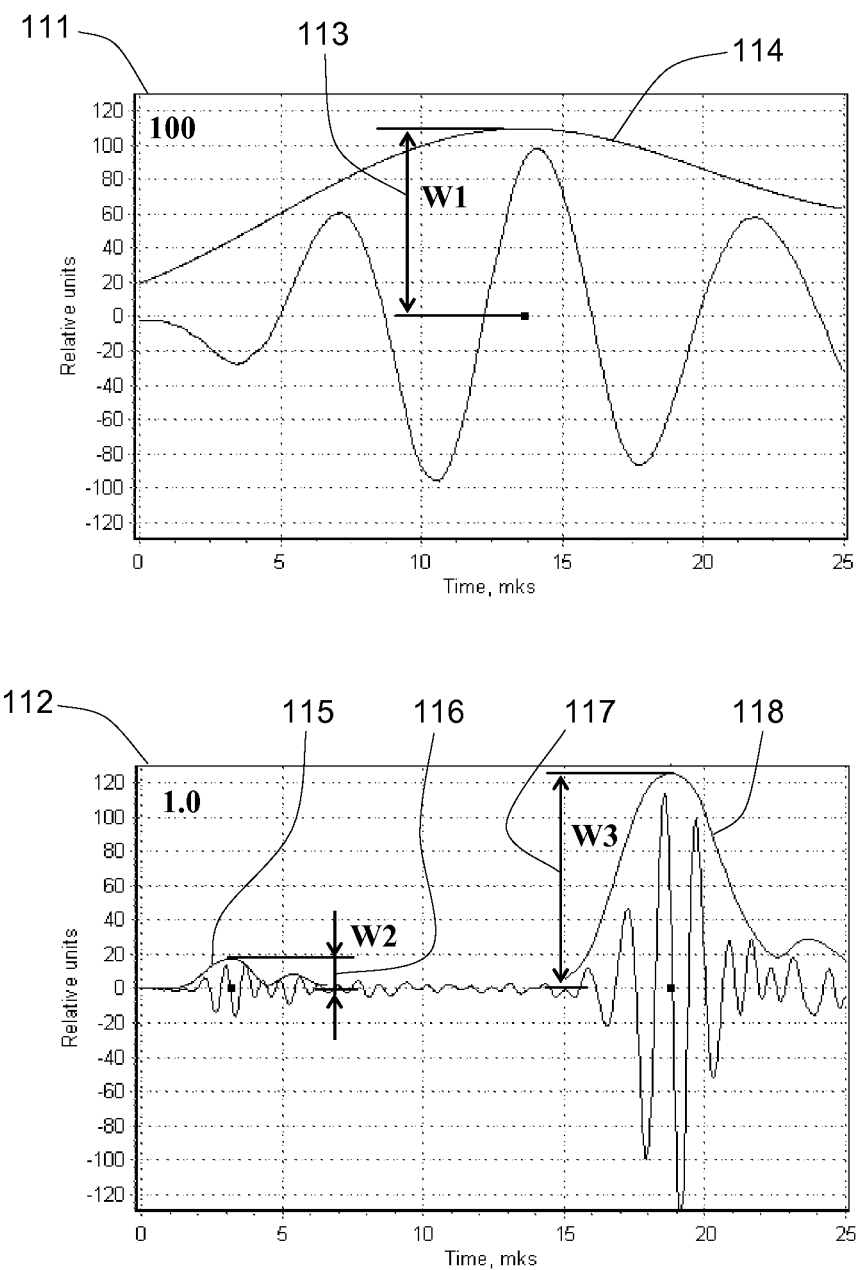
FIG. 11 illustrates the calculation of relative strength for signals related to low- and high-frequency waveforms used for determination of signals strength ratio.

FIG. 11 illustrates the calculation of relative strength for signals related to low- and high-frequency waveforms used for determination of signals strength ratio. Low-frequency and high-frequency signals displayed in panels 111 and 112 accordingly, were recorded simultaneously during a single measurement. Thus, influence of variations of probe contact pressure and contact condition on relative power ratios is eliminated. At low frequency, signal strength W1 is calculated as the peak amplitude 113 of the wavelet envelope 114 corresponding to the guided wave in the compact bone or bulk wave in the spongy bone. At high frequency, signal strengths W2 and W3 are determined as peak amplitudes 116 and 117 of the wavelet envelopes 115 and 118 related accordingly for the bulk and surface waves.

Figure 12:
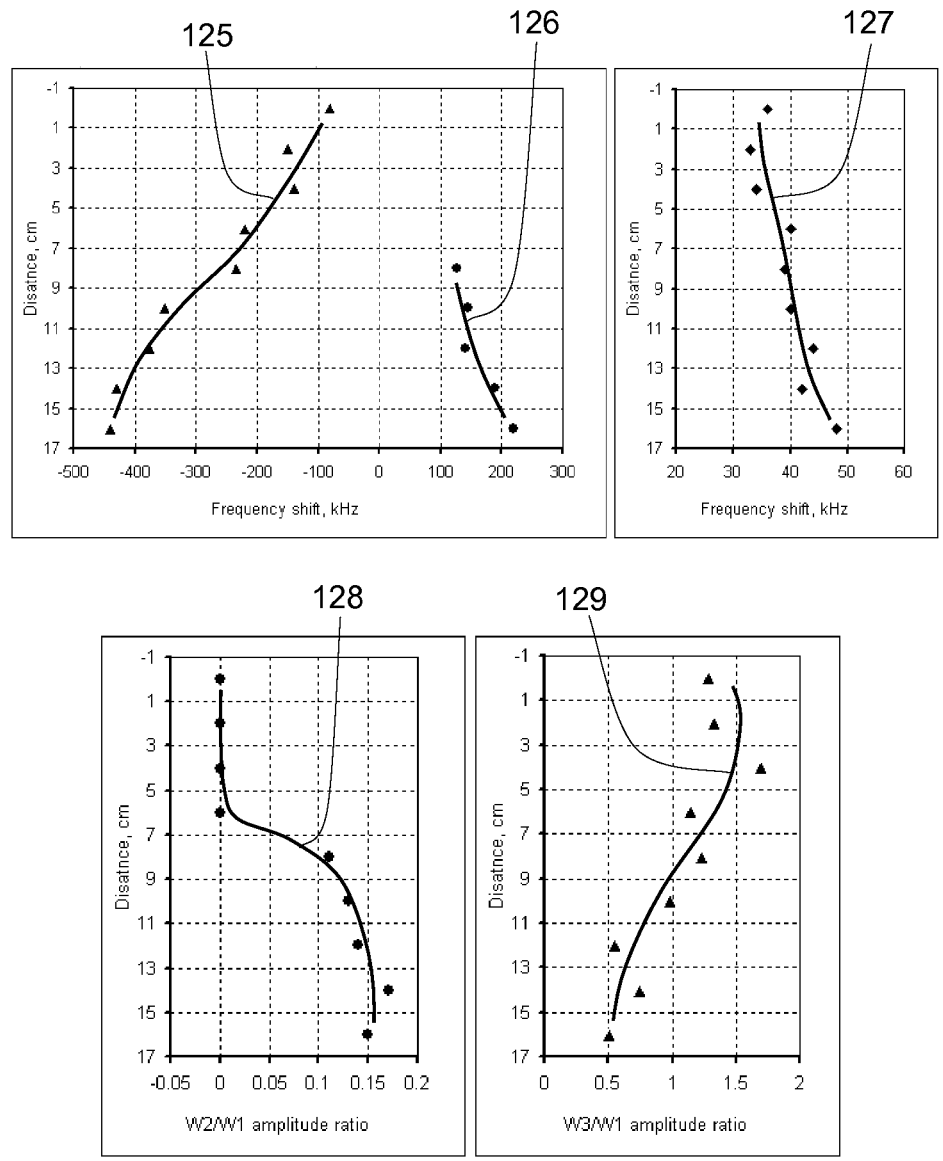
FIG. 12 presents a set of waveform parameters displayed in the form of profile graphs.

FIG. 12 represents a set of calculated axial profiles of the waveform parameters along a bone including:
1) 125—a profile of frequency shift for the high-frequency surface wave,
2) 126—a profile of frequency shift for the high-frequency longitudinal wave,
3) 127—a profile of frequency shift for the low-frequency guided wave,
4) 128—a profile of amplitudes ratio W2/W1 (see FIG. 8), and
5) 129—a profile of amplitudes ratio W3/W1 (see FIG. 9).

These profiles are also used for evaluation of the measurement data quality. It is assumed that a profile graph along a bone is a smooth line. Possible deviations of the measured parameters can be partly caused by signal noise, measurement error, poor contact of the ultrasound transducer with a skin surface or by improper probe handling. The standard deviation of the calculated parameters from the smooth curve is calculated for selected profile graphs and the obtained value serves as a "quality index" for the entire bone examination procedure. The quality index should be within certain predetermined limits to qualify the examination data as satisfactory. This index may also serve as a feedback for operator training.

Figure 13:
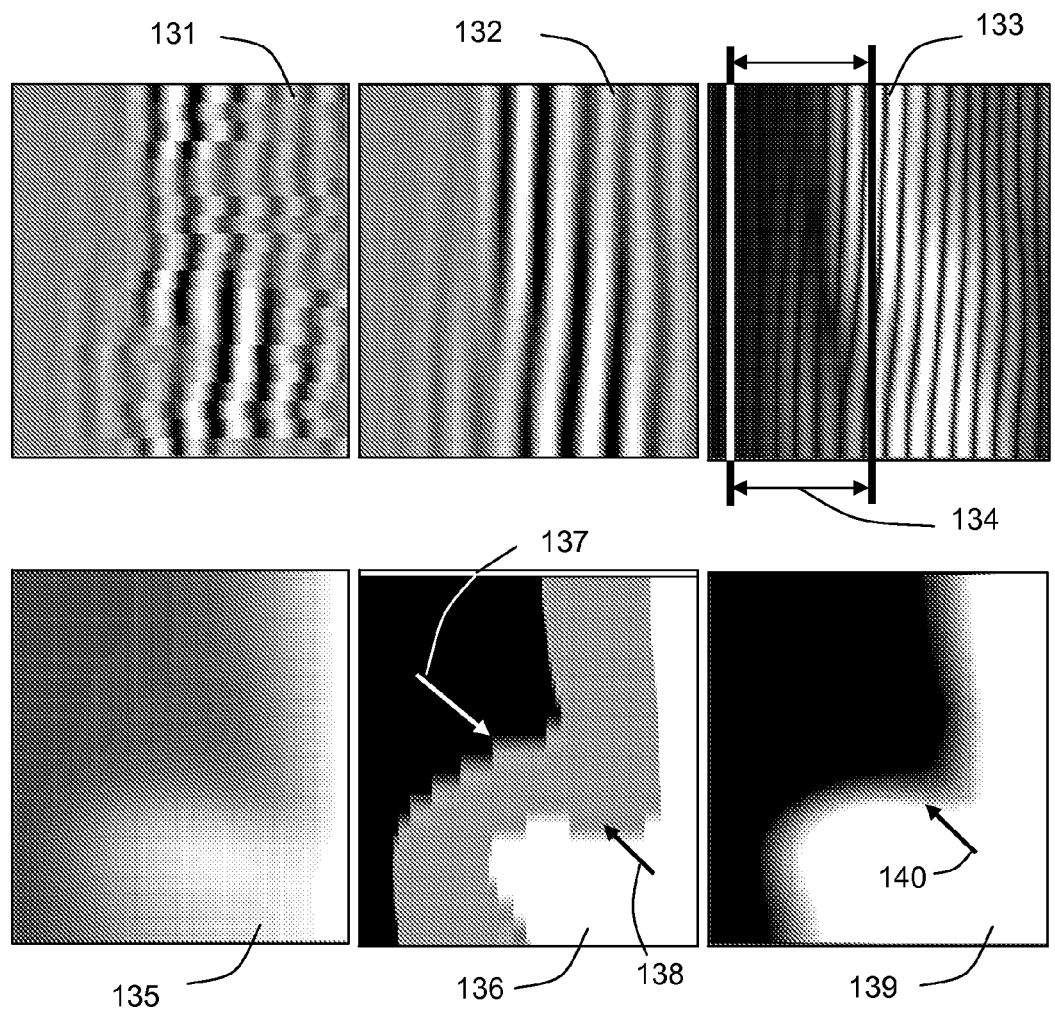
FIG. 13 is an illustration of processing of 2-D map of the received waveforms.

FIG. 13 illustrates steps of processing of a 2-D map of the received waveforms. Initial map 131 is composed of received ultrasonic signals. The vertical coordinate in the map 131 is the distance along the scanned trajectory, the horizontal coordinate is time, and the signal amplitude is depicted by the gray scale of the image. Map 132 is obtained by smoothing and interpolation of map 131. The interpolation procedure eliminates sharp deviations in the pattern. Smoothing is made by spatial filtering of the pattern and normalization of the amplitude in every signal line. Signal rectification for every line of the map 132 results in the map 133 which is then used for selection of the region of interest 134. This region of interest 134 is defined as an area of the map corresponding to the time interval with the most pronounced changes of the pattern. The pattern 135 is obtained by enveloping procedure or low pass filtering of the pattern in the region of interest 134. The pattern 136 is obtained by binarization of the pattern 135, where faster front 137 and slower front 138 of enveloped ultrasonic signals are determined by selecting two amplitude thresholds. The pattern 139 clearly showing the signal front profile 140 is obtained from the pattern 136 by adjusting the brightness and contrast.

Figure 14:
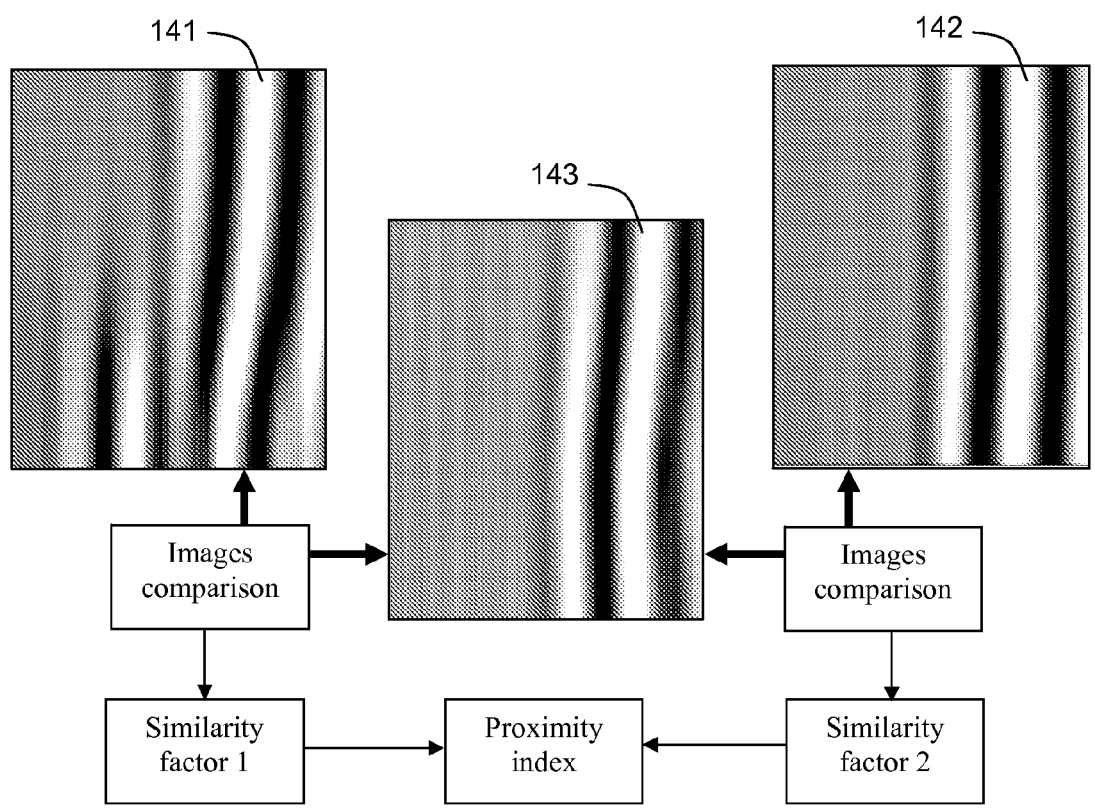
FIG. 14 is a chart showing the determination of proximity index.

FIG. 14 is a chart illustrating the determination of proximity indexes for assessment of bone conditions. Waveform maps 141 and 142, which are similar to map 132 obtained by the procedure illustrated in FIG. 10, are statistically mean waveform maps stored in the database on classified bone conditions. For example, the map 141 corresponds to tibia of young, healthy individuals, and the map 142 corresponds to tibia for an osteoporotic group of subjects at elderly age. Waveform map 143 obtained on the tibia of a patient is compared with maps 141 and 142 using images matching algorithms and then certain similarity factors are calculated. Proximity index is defined as the ratio of these factors, which show compliance of the waveform map 143 to the maps 141 or 142.

Figure 15:
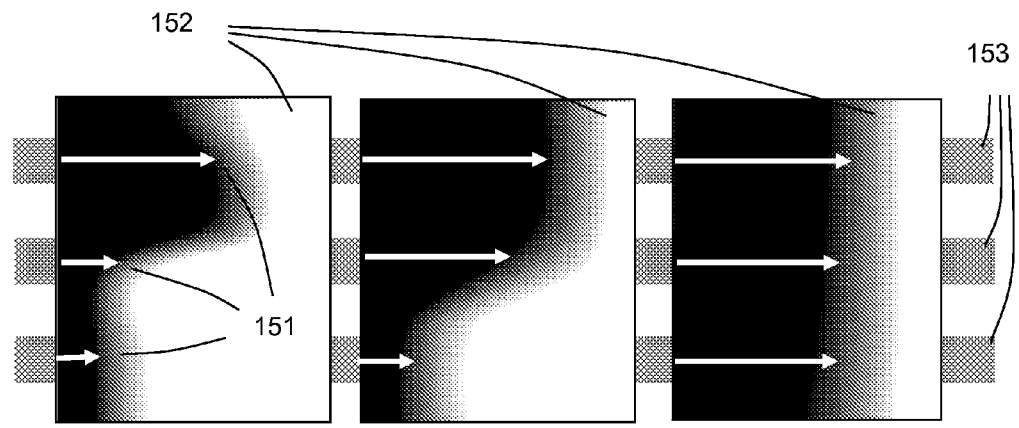
FIG. 15 is an illustration of assessment of bone osteopenia and osteoporosis using the data on axial profile of acoustic wave fronts.

FIG. 15 is an illustration of the use of received wave packet fronts for evaluating the stages of bone osteopenia and osteoporosis as progressing processes of bone degradation when it is developing along the bone length. Derivation of a wavefront profile (pattern 140) was illustrated above in FIG. 10. Wavefront profiles 151, 152 and 153 correspond to norm, osteopenia and osteoporosis, respectively. Zones 154, 155 and 156 are diagnostically informative zones of the wavefront profile. Signal arrival times 157, 158 and 159 shown by white arrows are quantitative characteristics of bone condition and pathologic processes.

Figure 16:
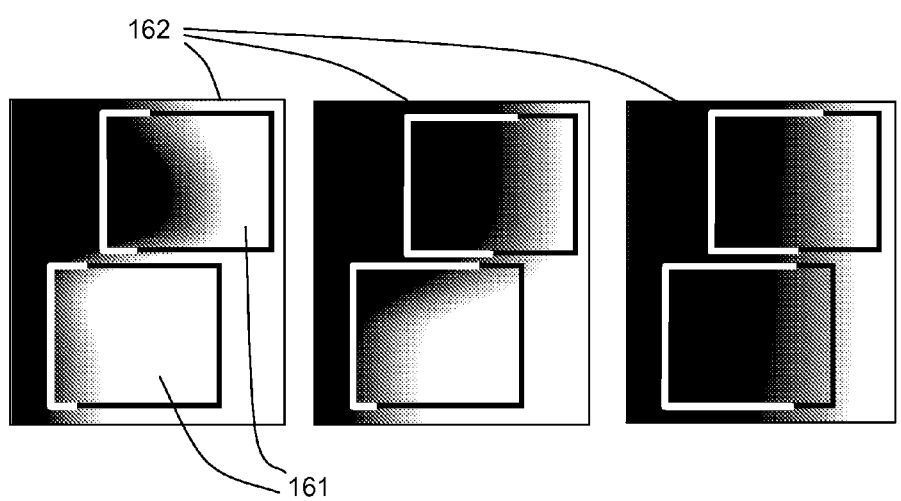
FIG. 16 is an illustration of assessment of signal fronts for evaluating the stages of bone osteopenia and osteoporosis using the data on signal intensities in predetermined informative areas of the axial profile.

FIG. 16 is an illustration of the use of signal strength for evaluating of stages of bone osteopenia and osteoporosis as progressing processes of bone degradation when it is developing along the bone length. Patterns 161, 162 and 163 correspond to norm, osteopenia and osteoporosis, respectively. Areas 164 and 165 are predetermined as diagnostically informative zones of the pattern. Average or integral intensities of areas 164 and 165 are quantitative characteristics of bone condition and pathologic processes.

Figure 17:
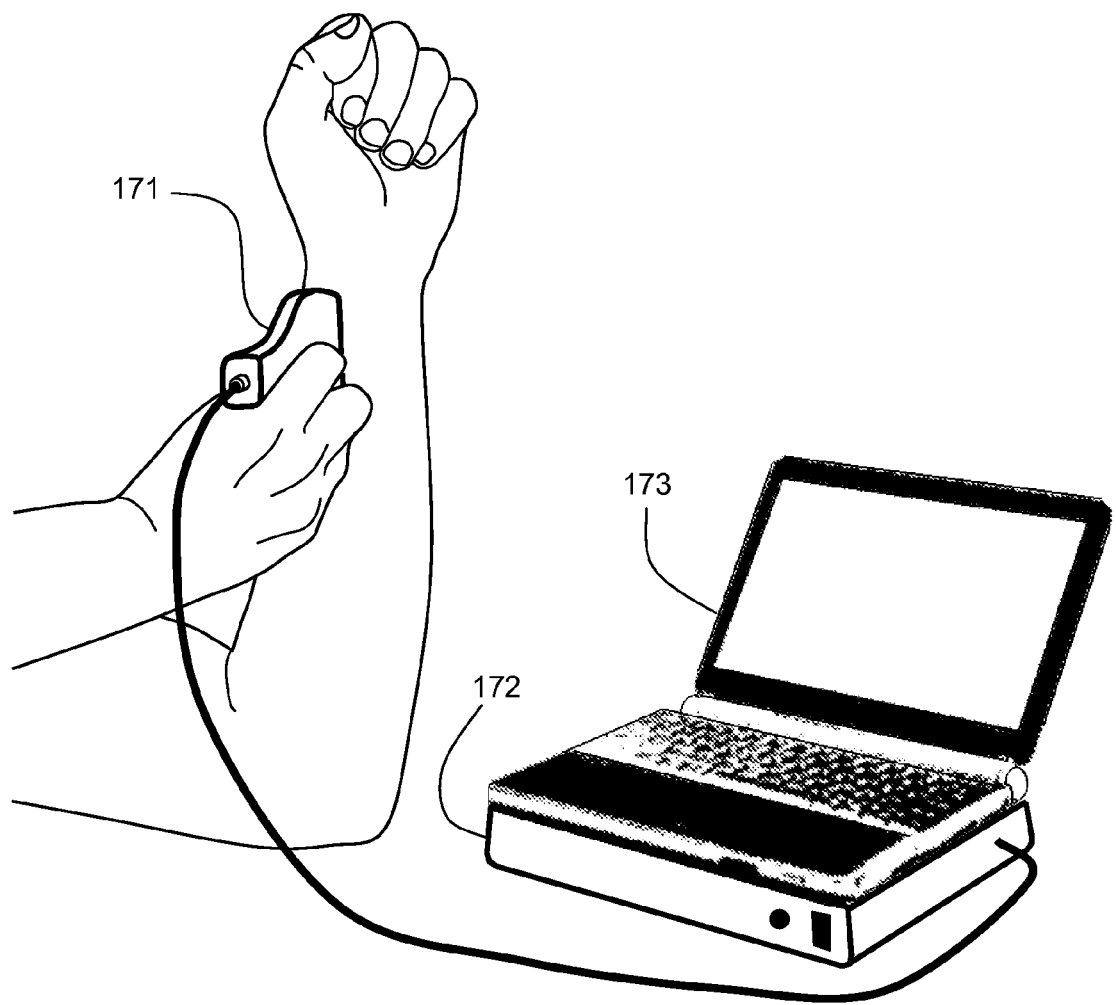
FIG. 17 is a perspective view of one embodiment of the apparatus for assessment of bone according to the present invention.

FIG. 17 is a perspective view of an embodiment of the apparatus for quantitative and non-invasive assessment of bone in the accordance with one aspect of the present invention. The apparatus comprises a hand-held ultrasonic scanning probe 171, an electronic unit 172 for excitation and acquisition of ultrasonic and position signals and a computer 173 as a data processor and display. An operator places the probe 171 on a skin surface above a patient's bone at a predefined starting anatomical reference point, then presses the probe against the bone to obtain the first record, and moves the probe step-by-step, repeating the measurements along the specified trajectory.

Figure 18:
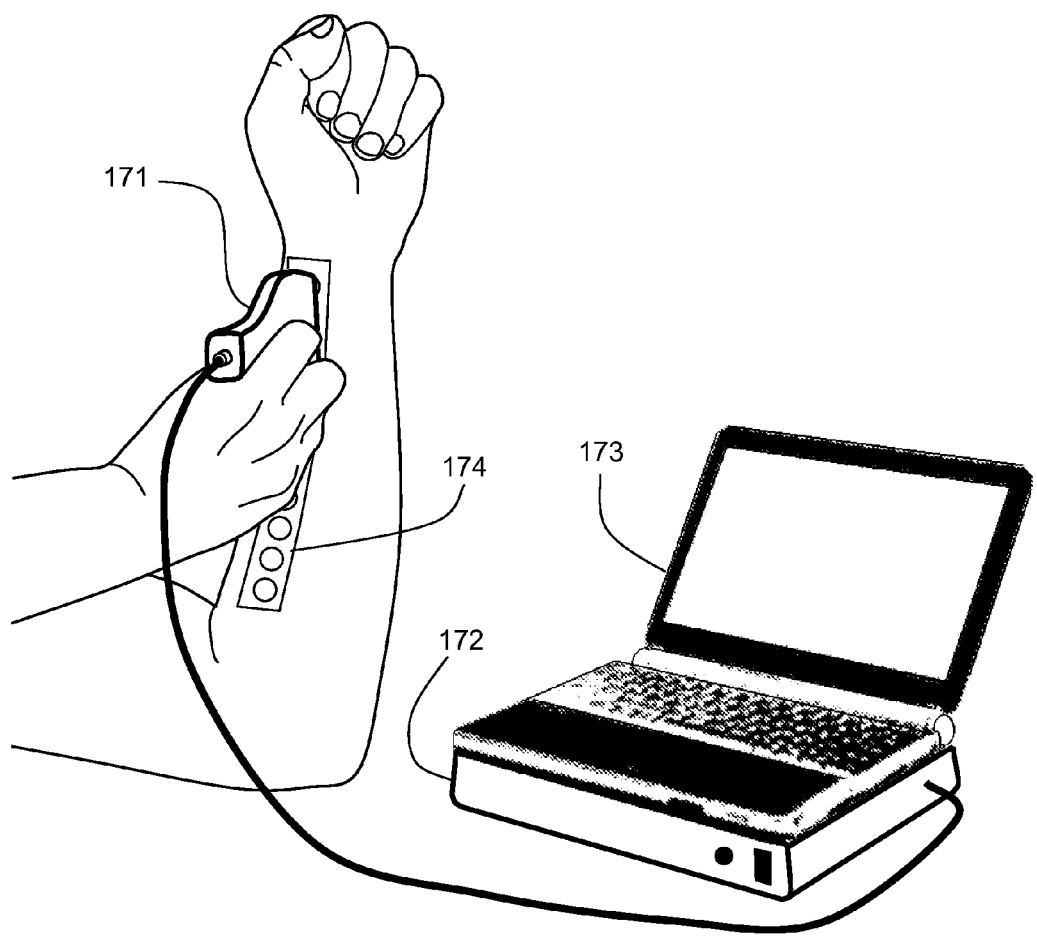
FIG. 18 is a perspective view of another embodiment of the apparatus for assessment of bone with positioning means made in the form of a tape with a series of holes defining the points of successive measurements along the chosen trajectory over the tested bone.

FIG. 18 is a perspective view of another embodiment of the apparatus where the probe positioning means is realized in the form of a tape with a series of markings (such as holes) defining the points of successive measurements along the chosen trajectory over the tested bone.

Figure 19:
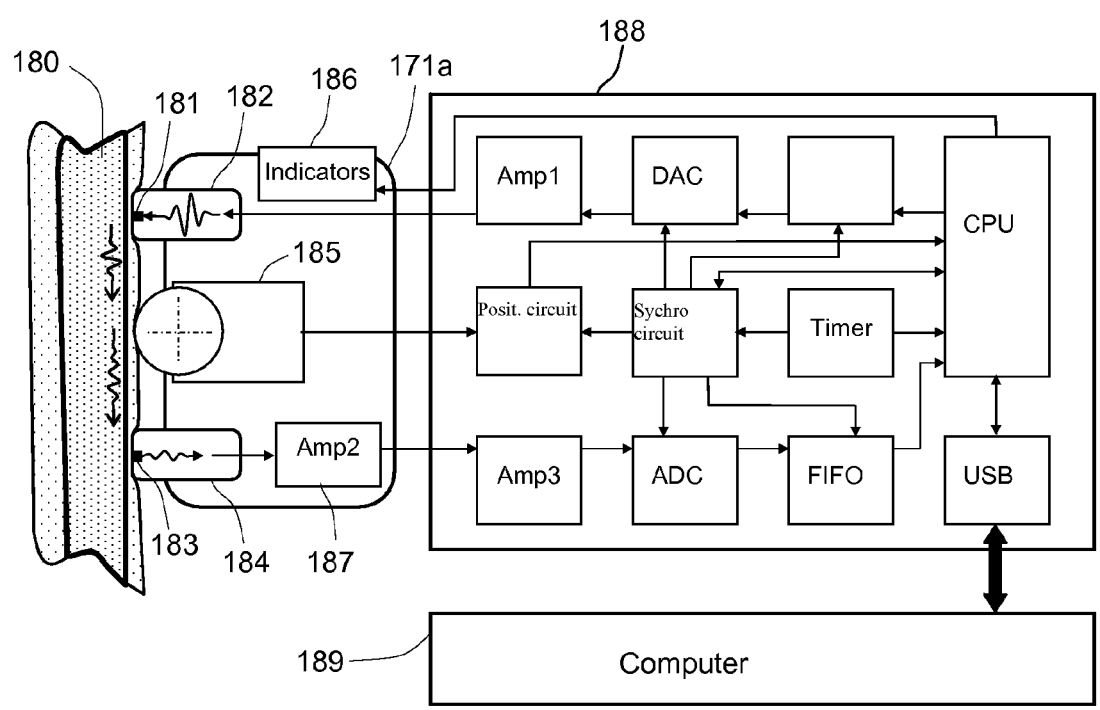
FIG. 19 is a block-diagram of yet another embodiment of the apparatus for assessment of bone according to the present invention.

FIG. 19 is a block-diagram of the apparatus for quantitative and non-invasive assessment of bone in the accordance with yet another aspect of the present invention. The ultrasonic scanning probe 171a being positioned on a skin surface above a bone 180 emits a series of broadband ultrasonic pulses through a thin layer of soft tissues by means of an ultrasonic transmitting transducer 182. An ultrasonic transducer 184 receives the ultrasonic signal passed through a bone 180. The acquired signal via the amplifier 187 is transmitted to an electronic unit 188. The probe 171a includes a distance metering means 185 realized in the form of a roller-based motion tracker. The motion tracker obviates the need for a tape as described above and allows monitoring and selecting proper successive locations for measurements based on a distance from a starting point. In a further improvement of this version of the device, a non-contact optical motion tracker similar to that used in the computer optical mouse can be employed.

An optional light emitting diode 186 is used to provide feedback to the operator about the amplitude of received ultrasonic signals to control the probe's applied force. The electronic unit 188 provides initial series of wave packets to transmitting transducer, acquires and processes the signals from the receiving transducer, acquires the data from the positioning system and communicates in real-time with the computer 189.

Figure 20:
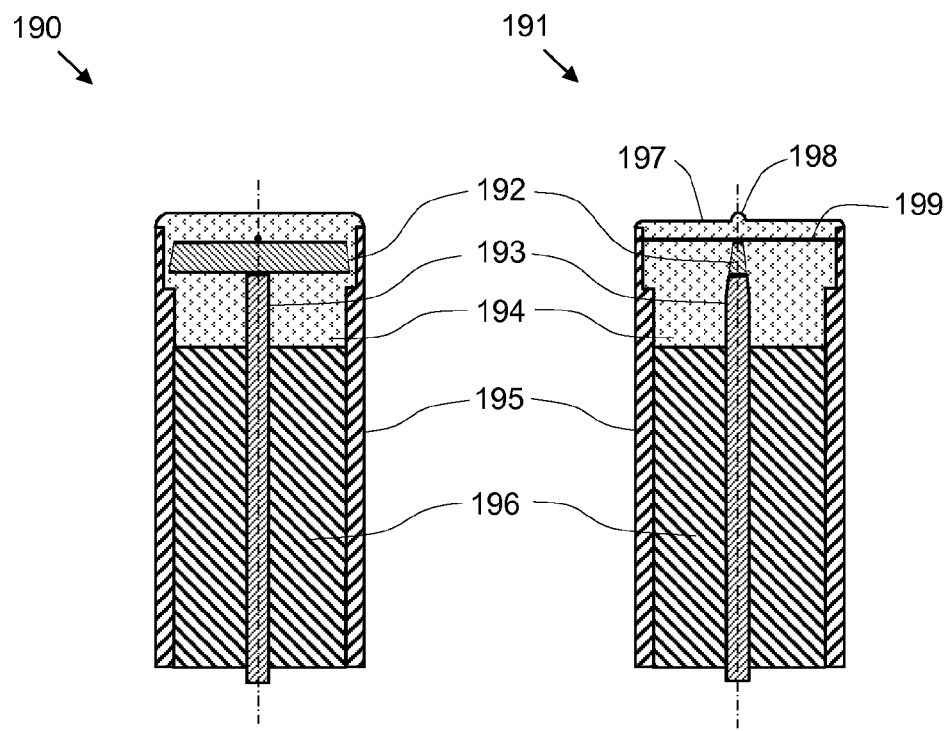
FIG. 20 shows two cross-sectional views of a broadband ultrasonic transducer in the accordance to the present invention; and finally

FIG. 20 shows two orthogonal cross-sections of a broadband ultrasonic transducer in accordance with the present invention. Frontal 190 and lateral 191 cross-sectional views are represented. The preferred design of a transducer consists of:

1) a miniature piezoceramic transducer 192 shaped as a prism with inclined facets pointing towards the bone and mounted on a metal support rod 193, which is a hot electrode connected to the output of the electronic unit;
2) a compound fill up 194 (for example, an epoxy compound);
3) a metal shield housing 195;
4) and an electrical insulation 196, for example, a Teflon cylinder.

A silver wire 199 connects the piezoceramic transducer 192 with the shield housing 195, which is used as the ground electrode. A skin contact surface 197 is flat with rounded edges to avoid local overpressure on the patient's body with a linear ridge 198 providing reliable acoustic contact with the tissue.

Figure 21:
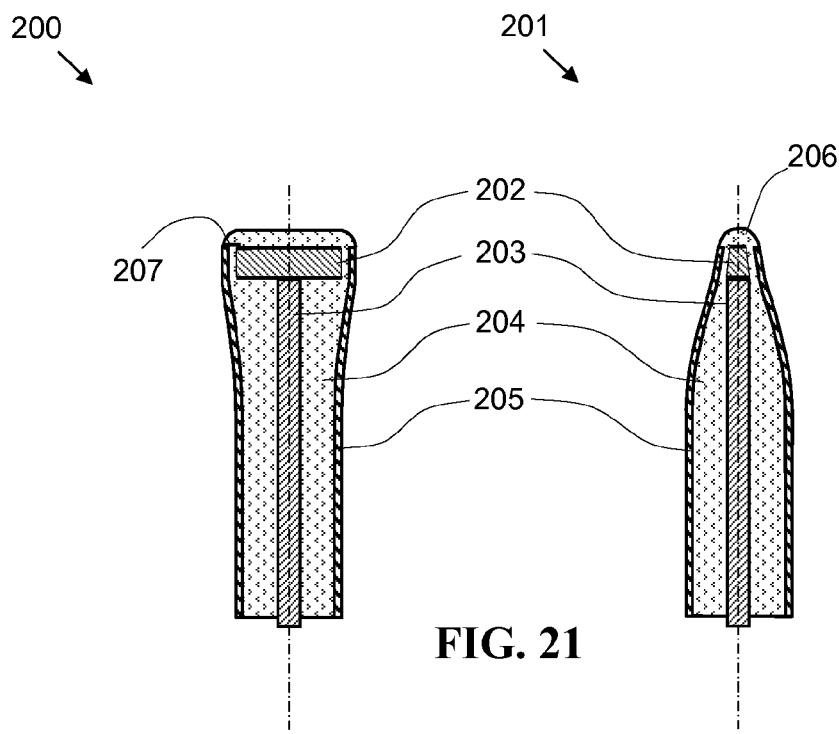
FIG. 21 shows two cross-sectional views of another broadband ultrasonic transducer in accordance to the present invention.

FIG. 21 shows two orthogonal cross-sections of another embodiment of a broadband ultrasonic transducer in accordance with the present invention. Frontal 200 and lateral 201 cross-sectional views are represented. The transducer consists of a miniature ellipsoidal prism-shaped piezoceramic element 202 with inclined facets pointing towards the bone. The piezoceramic element 202 is mounted on a metal support rod 203, which is a hot electrode connected to the output of the electronic unit. Inner transducer volume is filled up with a compound 204. A metal shield housing 205 provides mechanical protection of the transducer and is used as a ground electrode. A thin metal wire 206 connects the transducer 202 with the shield housing 205.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A method for quantitative non-invasive assessment of bone conditions comprising the steps of:
    (a) acoustically coupling of an ultrasonic probe with a body surface over the bone, said probe comprising a broadband emitting transducer and a broadband receiving transducer,
    (b) emitting a composite signal comprising a sequential train of ultrasonic wave packets of multiple carrier frequencies with predefined delays therebetween and propagating said wave packets in axial propagation mode along a predetermined trajectory on said bone with said broadband emitting transducer,
    (c) acquiring a train of ultrasonic signals from said broadband receiving transducer,
    (d) repeating the steps (a), (b) and (c) at various locations along said trajectory,
    (e) defining said probe positions along said trajectory at the same time as acquiring said series of ultrasonic signals,
    (f) calculating spatial profiles of selected parameters of the received waveforms for at least a portion of said bone, said step further including analyzing said acquired ultrasonic signals to determine portions thereof related to different modes of ultrasonic waves, said different modes defined as longitudinal, surface, and guided waves; calculating waveform parameter profiles for said determined portions related to different modes of ultrasonic waves; calculating of a quality index defined as deviation of calculated parameters from a predetermined smooth curve; wherein said quality index is provided as a feedback for an operator, said quality index indicating a degree of operator error in handling said probe during examination of said bone,
    (g) evaluating diagnostically relevant features of said spatial profiles, and
    (h) evaluating bone condition from said diagnostically relevant features of said spatial profiles.

2. The method as in claim 1, wherein said waveform parameter profile is composed by processing a 2-D map of said acquired ultrasonic signals; said step (h) further including calculating proximity indexes of said 2-D map of said acquired train of ultrasonic signals to predetermined statistically mean 2-D maps of ultrasonic signals indicating various bone conditions.

3. The method as in claim 2, wherein said predetermined maps include maps for assessment of various stages of osteopenia and osteoporosis.

* * * * *